United States Patent [19]

Clason et al.

[11] 4,417,990

[45] Nov. 29, 1983

[54] MIXED METAL SALTS/SULFURIZED PHENATE COMPOSITIONS AND LUBRICANTS AND FUNCTIONAL FLUIDS CONTAINING THEM

[75] Inventors: Donald L. Clason, Mentor; Calvin W. Schroeck, Eastlake, both of Ohio

[73] Assignee: The Lubrizol Corporation, Wickliffe, Ohio

[21] Appl. No.: 334,251

[22] Filed: Dec. 24, 1981

Related U.S. Application Data

[63] Continuation-in-part of Ser. No. 205,095, Nov. 7, 1980, Pat. No. 4,308,154, which is a continuation of Ser. No. 44,286, May 31, 1979, abandoned.

[51] Int. Cl.$^3$ ............................................... C10M 1/48
[52] U.S. Cl. ............................... 252/32.7 E; 252/35; 252/38; 252/42.7; 252/46.7; 252/400 R; 252/406
[58] Field of Search ...................... 252/32.7 E, 35, 38, 252/46.7, 42.7, 400, 406

[56] References Cited

U.S. PATENT DOCUMENTS

| | | | |
|---|---|---|---|
| 3,178,368 | 4/1965 | Hanneman | 252/42.7 |
| 3,437,595 | 4/1969 | Coupland | 252/42.7 |
| 3,523,081 | 8/1970 | Braid | 252/32.7 E |
| 3,625,893 | 12/1971 | Brook et al. | 252/32.7 E |
| 3,629,109 | 12/1971 | Gergel et al. | 252/327 E |
| 3,726,798 | 4/1973 | Silver | 252/75 |

*Primary Examiner*—Jacqueline V. Howard
*Attorney, Agent, or Firm*—Ronald L. Lyons; Raymond F. Keller

[57] ABSTRACT

A composition comprising (A) a mixed metal salt of (A)(I) at least one acid of formula I

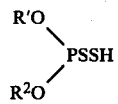

wherein R' and R$^2$ are the same or different and each of R' and R$^2$ is a hydrocarbon-based radical, and (A)(II) at least one aliphatic or alicyclic carboxylic acid containing from about 2 to about 40 carbon atoms; the ratio of equivalents of (A)(I) to (A)(II) being in the range of about 0.5:1 and about 400:1; and (B) at least one sulfurized Group II metal phenate; the weight ratio of (A) to (B) being in the range of about 40:1 to about 1:2. These compositions are useful in lubricants and functional fluids (such as hydraulic fluids) as antioxidants and extreme pressure agents having improved thermal stability.

35 Claims, No Drawings

MIXED METAL SALTS/SULFURIZED PHENATE COMPOSITIONS AND LUBRICANTS AND FUNCTIONAL FLUIDS CONTAINING THEM

REFERENCE TO RELATED APPLICATIONS

This application is a continuation-in-part of copending U.S. application Ser. No. 205,095 filed Nov. 7, 1980, now U.S. Pat. No. 4,308,154, which is a continuation of U.S. application Ser. No. 44,286 filed May 31, 1979, now abandoned. The disclosures of these prior applications are hereby incorporated by reference in this application in their entirety.

TECHNICAL FIELD

This invention relates to phosphorous- and sulfur-containing compositions of improved thermal stability useful in lubricants and functional fluids. More particularly, this invention relates to compositions comprising (A) mixed metal salts of (A)(I) at least one acid of formula I

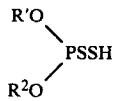

wherein each R' and R² is a hydrocarbon-based radical, and (A)(II) at least one aliphatic or alicyclic carboxylic acid; and (B) at least one sulfurized Group II metal phenate.

BACKGROUND OF THE INVENTION

The use of metal salts, especially zinc salts, of phosphorodithioic acids as antioxidants and extreme agents in lubricants and functional fluids has been known for some time. However, the environment in which such lubricants and functional fluids are used has become increasingly severe over recent years with the further development of machinery employing such lubricants and functional fluids. It is important, therefore, that materials of this type be developed which have higher thermal stability than has previously been the case.

The use of sulfurized calcium alkyl phenates as compounding agents in lubricating oils to inhibit corrosion, piston ring sticking and gum formation in internal combustion engines resulting from oxidation of lubricating oil and polymerization of engine fuel residues is also known, as indicated in U.S. Pat. Nos. 2,680,096 and 3,036,971.

SUMMARY OF THE INVENTION

This invention contemplates the provision of a composition that comprises (A) a mixed metal salt of (A)(I) at least one acid of formula I

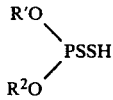

wherein each of R' and R² is a hydrocarbon-based radical, and (A)(II) at least one aliphatic or alicyclic carboxylic acid; the ratio of equivalents of (A)(I) to (A)(II) being in the range of about 0.5:1 to about 400:1; and (B) at least one sulfurized Group II metal phenate; the ratio in parts by weight of (A) to (B) being in the range of about 40:1 to about 1:2

An object of the present invention is the provision of compositions containing phosphorus, sulfur and metal which have high thermal stability and which also provide antioxidant and extreme pressure improving properties to lubricants and functional fluids.

A further object is to provide for the incorporation of relatively large amounts of metal in such compositions.

Still another object is to provide improved lubricants and functional fluids, especially hydraulic fluids.

Other objects will be apparent to those skilled in the art from the following description of the preferred embodiment.

DESCRIPTION OF THE PREFERRED EMBODIMENT

The compositions of the present invention comprise mixtures of (A) mixed metal salts of (A)(I) at least one acid of formula I

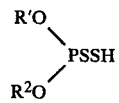

wherein each R' and R² is independently a hydrocarbon based radical, and (A)(II) at least one aliphatic or alicyclic carboxylic acid, the ratio of (A)(I) to (A)(II) being in the range of about 0.5:1 to about 400:1; and (B) at least one sulfurized Group II metal phenate; the weight ratio of (A) to (B) being in the range of about 40:1 to about 1:2, preferably about 20:1 to about 1:1; and advantageously about 15:1 to about 5:1. When the compositions of the present invention are used in lubricants, as discussed below, a preferred ratio of (A) to (B) is about 1:1. On the other hand, when these compositions are used in functional fluids, such as hydraulic fluids, as discussed below, a preferred ratio of (A) to (B) is about 14:1.

The term "hydrocarbon-based radical" is used throughout this specification and in the appended claims to denote a radical having a carbon atom directly attached to the remainder of the molecule and having predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, the two indicated substituents may together form a cyclic radical). Such radicals are known to those skilled in the art; examples include methyl, ethyl, butyl, hexyl, octyl, decyl, dodecyl, tetradecyl, octadecyl, eicosyl, cyclohexyl, phenyl and naphthyl (all isomers being included).

(2) Substituted hydrocarbon radicals; that is, radicals containing non-hydrocarbon substituents which, in the context of this invention, do not alter predominantly hydrocarbon character of the radical. Those skilled in the art will be aware of suitable substituents (e.g., halo, hydroxy, alkoxy, carbalkoxy, nitro, alkylsulfoxy).

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based radical.

(A) THE MIXED METAL SALTS

Component (A) includes the mixed metal salts of the Group I metals, the Group II metals, aluminum, tin, cobalt, lead, molybdenum, manganese and nickel, as well as mixtures of two or more of those metals. The preferred salts are those of zinc. As will be apparent from the foregoing, the mixed metal salts of this invention are salts of at least two acidic components of which component (A)(I) is a phosphorodithioic acid and component (A)(II) is at least one aliphatic or alicyclic carboxylic acid.

Preferably, the hydrocarbon-based radicals in the compounds useful as component (A)(I) according to this invention are free from acetylenic and usually also from ethylenic unsaturation and have from about 3 to about 50 carbon atoms, preferably from about 3 to about 18 carbon atoms. $R'$ and $R^2$ are most often identical, although they may be different and either or both may be mixtures. The radicals are usually hydrocarbon, preferably alkyl, and most desirably branched alkyl.

Component (A)(II) may be a monocarboxylic or polycarboxylic acid, usually containing from 1 to about 3 carboxy groups and preferably only 1. It may contain from about 2 to about 40, preferably from about 2 to about 20 carbon atoms, and advantageously about 5 to about 20 carbon atoms. The preferred carboxylic acids are those having the formula $R^3COOH$, wherein $R^3$ is an aliphatic or alicyclic hydrocarbon-based radical preferably free from acetylenic unsaturation. Suitable acids include the butanoic, pentanoic, hexanoic, octanoic, nonanoic, decanoic, dodecanoic, octadecanoic and eicosanoic acids, as well as olefinic acids such as oleic, linoleic, and linolenic acids and linoleic acid dimer. For the most part, $R^3$ is a saturated aliphatic radical and especially a branched alkyl radical such as the isopropyl or 3-heptyl radical. Illustrative polycarboxylic acids are succinic, alkyl- and alkenylsuccinic, adipic, sebacic and citric acids.

Component (A) may be prepared by merely blending a metal salt of component (A)(I) with a metal salt of component (A)(II) in the desired ratio. This ratio is between about 0.5:1 and about 400:1 on an equivalent weight basis. Preferably, the ratio is between about 0.5:1 and about 200:1. Advantageously, the ratio of (A) to (B) can be from about 0.5:1 to about 100:1, preferably from about 0.5:1 to about 50:1, and more preferably from about 0.5:1 to about 20:1. Further, the ratio of (A) to (B) can be from about 0.5:1 to about 4.5:1, preferably about 2.5:1 to about 4.25:1. For this purpose, the equivalent weight of a phosphorodithioic acid is its molecular weight divided by the number of —PSSH groups therein, and that of a carboxylic acid is its molecular weight divided by the number of carboxy groups therein.

A second and preferred method for preparing the mixed metal salts of this invention is to prepare a mixture of the acids (components (A)(I) and (A)(II)) in the desired ratio and to react the acid mixture with a suitable metal base. When this method of preparation is used, it is frequently possible to prepare a salt containing an excess of metal with respect to the number of equivalents of acid present; thus, mixed metal salts containing as many as 2 equivalents and especially up to about 1.5 equivalents of metal per equivalent of acid may be prepared. The equivalent of a metal for this purpose is its atomic weight divided by its valence.

Variants of the above-described methods may also be used to prepare the mixed metals salts of this invention. For example, a metal salt of component (A)(I) or (A)(II) may be blended with the free carboxylic acid as component (A)(II) or (A)(I), respectively, and the resulting blend reacted with additional metal base.

Suitable metal bases for the preparations of the mixed metal salts of this invention include the free metals previously enumerated and their oxides, hydroxides, alkoxides and basic salts. Examples are sodium hydroxide, sodium methoxide, sodium carbonate, potassium hydroxide, potassium carbonate, magnesium oxide, magnesium hydroxide, calcium hydroxide, calcium acetate, zinc oxide, zinc acetate, lead oxide, nickel oxide and the like.

The temperature at which the mixed metal salts of this invention are prepared is generally between about 30° and about 150° C., preferably up to about 125° C. If the mixed salts are prepared by neutralization of a mixture of acids with a metal base, it is preferred to employ temperatures above about 50° and especially above about 75°. It is frequently advantageous to conduct the reaction in the presence of a substantially inert, normally liquid organic diluent such as naphtha, benzene, xylene, mineral oil or the like. If the diluent is mineral oil or is physically and chemically similar to mineral oil, it frequently need not be removed before using the mixed metal salt as an additive for lubricants or functional fluids.

The preparation of the mixed salts of this invention is illustrated by the following examples. All parts and percentages are by weight.

EXAMPLE 1

A mixture of 67 parts (1.63 equivalents) of zinc oxide and 48 parts of mineral oil is stirred at room temperature and a mixture of 401 parts (1 equivalent) of di-(2-ethylhexyl)phosphorodithioic acid and 36 parts (0.25 equivalent) of 2-ethylhexanoic acid is added over 10 minutes. The temperature increases to 40° C. during the addition. When addition is complete, the temperature is increased to 80° C. for 3 hours. The mixture is then vacuum stripped at 100° C. to yield the desired mixed metal salt as a 91% solution in mineral oil.

EXAMPLE 2

Following the procedure of Example 1, a product is prepared from 383 parts (1.2 equivalents) of a dialkyl phosphorodithioic acid containing 65% isobutyl and 35% amylgroups, 43 parts (0.3 equivalent) of 2-ethylhexanoic acid, 71 parts (1.73 equivalents) of zinc oxide and 47 parts of mineral oil. The resulting mixed metal salt, obtained as a 90% solution in mineral oil, contains 11.07% zinc.

EXAMPLE 3

Following the procedure of Example 1, a product is prepared from 474 parts (1.2 equivalents) of a dialkylphosphorodithioic acid containing 80% 2-ethylhexyl groups and 20% isobutyl groups, 43 parts (0.3 equivalent) of 2-ethylhexanoic acid, 80 parts (1.95 equivalents) of zinc oxide and 57 parts of mineral oil. The resulting mixed metal salt is obtained as a 91% solution in mineral oil.

EXAMPLE 4

A mixture of 118 parts (2.8 equivalents) of zinc oxide, 25 parts (0.25 equivalent) of sebacic acid and 72 parts of mineral oil is stirred at room temperature and a mixture of 584 parts (2 equivalents) of the dialkylphosphorodithioic acid of Example 2 and 36 parts (0.25 equivalent) of 2-ethyl-hexanoic acid is added over 30 minutes. The temperature increases to 65° C. during the addition. The solution is heated to 80° C. for 3 hours and vacuum stripped at 108° C. The residue is filtered to yield the desired mixed metal salt (90% solution in mineral oil) containing 11.7% zinc.

EXAMPLE 5

A product is prepared by the procedure of Example 1 except that an equivalent amount of oleic acid is substituted for the 2-ethylhexanoic acid.

(B) THE SULFURIZED GROUP II METAL PHENATES

The sulfurized Group II metal phenates that are used in accordance with the present invention are preferably basic sulfurized Group II metal phenates. The phenol group of such phanates includes an aromatic moiety with at least one hydrocarbon-based radical and an oxygen atom attached to such aromatic moiety, as indicated in formula II, below. The phenol group is sulfurized and based (or overbased) with a Group II metal, as discussed below, to form component (B). As used herein, the term "normal" sulfurized Group II metal phenates is used to refer to those phenates wherein the ratio of Group II metal to the phenol group is about 1:2, in accordance with formula II $(R_a\text{—Ar—O—})_2 M$ 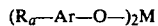 II wherein $(R_a\text{—Ar—O—})$ is the phenol group; M is a Group II metal; Ar is an aromatic moiety which is preferably benzene; R is a hydrocarbon-based radical; and a is an integer of from 1 up to the number of unsatisfied valences in Ar, preferably 1 or 2. As used herein, the term "basic" sulfurized Group II metal phenates refers to sulfurized Group II metal phenates wherein the ratio of Group II metal to the phenol group is greater than that of normal sulfurized Group II metal phenates. Such phenates are referred to interchangeably as "basic" or "overbased." Component (B) generally contains up to about 1000%, preferably up to about 500%, of the Group II metal present in the corresponding sulfurized normal Group II metal phenate. Advantageously, component (B) contains from about 250% to about 450%, preferably about 350%, of the Group II metal present in the corresponding sulfurized normal Group II metal phenate. Component (B) has a sulfur to phenol group molar ratio of from about 2:1 to about 1:2, preferably about 2:1 to about 1:1, and advantageously about 4:3. Any of the Group II metals can be used to form component (B), but calcium is preferred. Component (B) includes, for example, basic sulfurized tetrapropenyl phenate with, for example, about 230% or 380% of the calcium present in the corresponding normal calcium phenate, and a sulfur to phenol group molar ratio of about 4:3.

While the terms "phenol" and "phenate" are used herein in the description of component (B), it is to be understood that such terms are not intended to limit the aromatic moiety of the phenol group of component (B) to benzene. Accordingly, it is to be understood that the aromatic moiety of component (B), as represented by "Ar" in formula II can be a single aromatic nucleus such as a benzene nucleus, a pyridine nucleus, a thiophene nucleus, a 1,2,3,4-tetrahydronaphthalene nucleus, etc., or a polynuclear aromatic moiety. Such polynuclear moieties can be of the fused type; that is, wherein at least one aromatic nucleus is fused at two points to another nucleus such as found in naphthalene, anthracene, the azanaphthalenes, etc. Alternatively, such polynuclear aromatic moieties can be of the linked type wherein at least two nuclei (either mono- or polynuclear) are linked through bridging linkages to each other. Such bridging linkages can be chosen from the group consisting of carbon-to-carbon single bonds, ether linkages, keto linkages, sulfide linkages, polysulfide linkages of 2 to 6 sulfur atoms, sulfinyl linkages, sulfonyl linkages, methylene linkages, alkylene linkages, di-(lower alkyl)-methylene linkages, lower alkylene ether linkages, alkylene keto linkages, lower alkylene sulfur linkages, lower alkylene polysulfide linkages of 2 to 6 carbon atoms, amino linkages, polyamino linkages and mixtures of such divalent bridging linkages. In certain instances, more than one bridging linkage can be present in Ar between aromatic nuclei. For example, a fluorene nucleus has two benzene nuclei linked by both a methylene linkage and a covalent bond. Such a nucleus may be considered to have 3 nuclei but only two of them are aromatic. Normally, however, Ar will contain only carbon atoms in the aromatic nuclei per se (plus any lower alkyl or alkoxy substituent present).

The number of aromatic nuclei, fused, linked or both, in Ar can play a role in determining the integer values of a in formula II. For example, when Ar contains a single aromatic nucleus, a, is from 1 to 5. When Ar contains two aromatic nuclei, a can be an integer of 1 to 10. With a tri-nuclear Ar moiety, a can be an integer of 1 to 15. The value of a is obviously limited by the fact that it cannot exceed the total unsatisfied valences of Ar.

The single ring aromatic nucleus which can be the Ar moiety can be represented by the general formula $ar(Q)_m$ 

wherein ar represents a single ring aromatic nucleus (e.g., benzene) of 4 to 10 carbons, each Q independently represents a lower alkyl group, lower alkoxy group, nitro group, or halogen atom, and m is 0 to 3. As used in this specification and appended claims, "lower" refers to groups having 7 or less carbon atoms such as lower alkyl and lower alkoxy groups. Halogen atoms include fluorine, chlorine, bromine and iodine atoms; usually, the halogen atoms are fluorine and chlorine atoms.

Specific examples of single ring Ar moieties are the following:

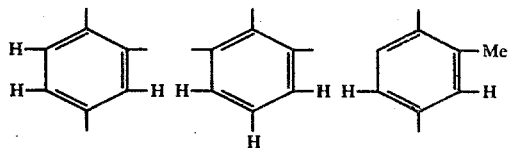

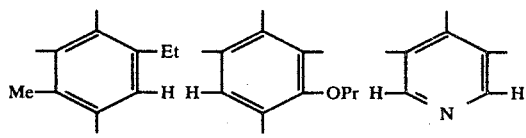

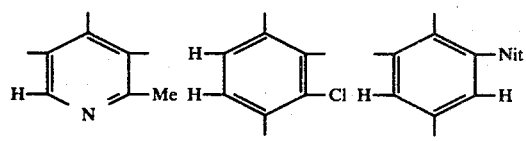

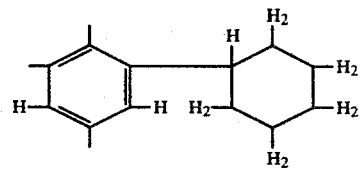

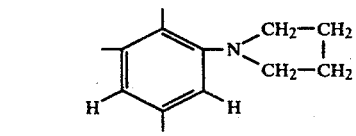

wherein Me is methyl, Et is ethyl, Pr is n-propyl, and Nit is nitro.

When Ar is a polynuclear fused-ring aromatic moiety, it can be represented by the general formula $$ar\mathbin{\diamondsuit} ar\mathbin{\diamondsuit}_{m'}(Q)_{mm'}$$

wherein ar, Q and m are as defined hereinabove, m' is 1 to 4 and ⊃ represent a pair of fusing bonds fusing two rings so as to make two carbon atoms part of the rings of each of two adjacent rings. Specific examples of fused ring aromatic moieties Ar are:

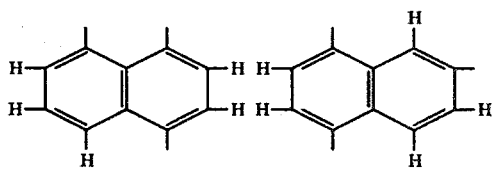

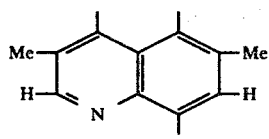

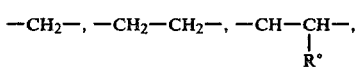

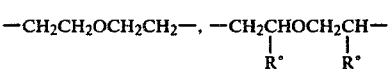

When the aromatic moiety Ar is a linked polynuclear aromatic moiety it can be represented by the general formula $$ar\text{-}(Lng\text{-}ar\text{-})_w(Q)_{mw}$$

wherein w is an integer of 1 to about 20, ar is as described above with the priviso that there are at least 2 unsatisfied (i.e., free) valences in the total of ar groups, Q and m are as defined hereinbefore, and each Lng is a bridging linkage individually chosen from the group consisting of carbon-to-carbon single bonds, ether linkages e.g. —O—), keto linkages (e.g., $$-\overset{\overset{\displaystyle O}{\|}}{C}-),$$

sulfide linkages (e.g., —S—), polysulfide linkages of 2 to 6 sulfur atoms (e.g., —S$_{2-6}$—), sulfinyl linkages (e.g., —S(O)—), sulfonyl linkages (e.g., —S(O)$_2$—), lower alkylene linkages (e.g., $$-CH_2-, -CH_2-CH_2-, -CH-CH-,\\ \quad\quad\quad\quad\quad\quad\quad\quad\quad\quad\quad | \\ \quad\quad\quad\quad\quad\quad\quad\quad\quad\quad\quad R°$$

etc.), di(lower alkyl)-methylene linkages (e.g., CR°$_2$—), lower alkylene ether linkages (e.g., $$-CH_2O-, -CH_2O-CH_2-, -CH_2-CH_2-O-,$$

$$-CH_2CH_2OCH_2CH_2-, -CH_2CHOCH_2CH-\\ \quad\quad\quad\quad\quad\quad\quad\quad\quad\quad\quad | \quad\quad\quad\quad | \\ \quad\quad\quad\quad\quad\quad\quad\quad\quad\quad\quad R° \quad\quad\quad R°$$

$$-CH_2CHOCHCH_2-,\\ \quad\quad\quad | \quad\quad | \\ \quad\quad\quad R° \quad\quad R°$$

etc.), lower alkylene sulfide linkages (e.g., wherein one or more —O—'s in the lower alkylene ether linkages is replaced with an —S— atom), lower alkylene polysulfide linkages (e.g., wherein one or more —O—'s is replaced with a —S$_{2-6}$ group), amino linkages (e.g.,

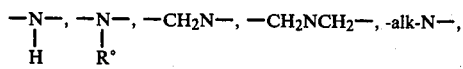

where alk is lower alkylene, etc.), polyamino linkages (e.g.,

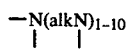

where the unsatisfied free N valences are taken up with H atoms or R° groups), and mixtures of such bridging linkages (each R° being a lower alkyl group). It is also possible that one or more of the ar groups in the above-linked aromatic moiety can be replaced by fused nuclei such as ar ⌬ ar ⌬ $_{m'}$.

Specific examples of linked moieties are:

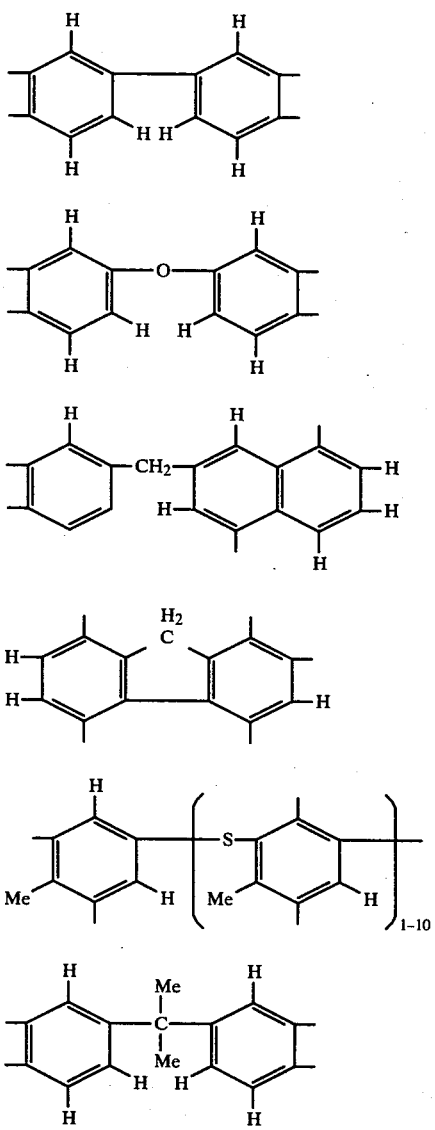

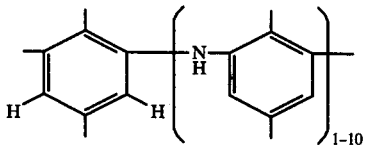

Usually all these Ar moieties are unsubstituted except for the R and —O— groups (and any bridging groups).

For such reasons as cost, availability, performance, etc., the Ar moiety is normally a benzene nucleus, lower alkylene bridged benzene nucleus, or a naphthalene nucleus.

As indicated in formula II, component (B) includes R, a hydrocarbon-based radical, directly bonded to the aromatic moiety Ar. Hydrocarbon-based radical R is defined above and contains about 6 to about 80 carbon atoms, preferably about 6 to about 30 carbons, more preferably about 8 to about 25 carbon atoms, and advantageously about 8 to about 15 carbon atoms. Examples of such hydrocarbon-based radicals R include propylene tetramer and tri(isobutene). The attachment of the hydrocarbon-based group R to the aromatic moiety Ar of component (B) of this invention can be accomplished by a number of techniques well known to those skilled in the art. One particularly suitable technique is the Friedel-Crafts reaction, wherein an olefin (e.g., a polymer containing an olefinic bond), or halogenated or hydrohalogenated analog thereof, is reacted with a phenol. The reaction occurs in the presence of a Lewis acid catalyst (e.g., boron trifluoride and its complexes with ethers, phenols, hydrogen fluoride, etc., aluminum chloride, aluminum bromide, zinc dichloride, etc.). Methods and conditions for carrying out such reactions are well known to those skilled in the art. See, for example, the discussion in the article entitled, "Alkylation of Phenols" in "Kirk-Othmer Encyclopedia of Chemical Technology," Second Edition, Vol. 1, pages 894-895, Interscience Publishers, a division of John Wiley and Company, New York, 1963. Other equally appropriate and convenient techniques for attaching the hydrocarbon-based group R to the aromatic moiety Ar will occur readily to those skilled in the art.

As will be appreciated from inspection of formula II the phenol group of component (B) of this invention contains at least one R group as defined above, and —O—. Each of the foregoing must be attached to a carbon atom which is a part of an aromatic nucleus in the Ar moiety. They need not, however, each be attached to the same aromatic ring if more than one aromatic nucleus is present in the Ar moiety.

The preparation of component (B) can be accomplished by any of the standard techniques known to those skilled in the art for producing basic sulfurized Group II metal phenates. These techniques include, for example, one-step processes wherein sulfurization and basing (or overbasing) with the Group II metal are effected simultaneously, and two-step processes wherein the phenol is first sulfurized, then based. Each of these techniques are well known to those skilled in the art and, accordingly, need not be further discussed herein. The source of sulfur is generally elemental sulfur, or sulfur halide, for example, SCl$_2$ or S$_2$Cl$_2$. Examples of patents disclosing suitable procedures for preparing Component (B) include U.S. Pat. Nos. 2,680,096;

3,036,971; 3,178,368; 3,437,595; and Re. 29,661, these patents being incorporated herein by reference.

Components (A) and (B) can be blended together in any suitable manner and then admixed, for example, with a diluent to form a concentrate as discussed below, or with a lubricant or functional fluid, as discussed below. Alternatively, components (A) and (B) can be admixed separately with such diluent, lubricant or functional fluid. The blending technique for mixing components (A) and (B) with each other is not critical and can be effected using any standard technique, depending upon the specific nature of the materials employed. In most instances, components (A) and (B) are liquids that are miscible with each other and, accordingly, can be readily mixed. In general, blending can be accomplished at room temperature. However, in instances wherein the viscosity of either component (A) or (B) is relatively high, blending can be facilitated by heating the components.

As previously indicated, the compositions of the present invention are useful as additives for lubricants and functional fluids, in which they function primarily as antioxidants and extreme pressure agents having improved thermal stability as compared with ordinary phosphorodithioic acid salts. They can be employed in a variety of lubricants based on diverse oils of lubricating viscosity, including natural and synthetic lubricating oils and mixtures thereof. The lubricants include crankcase lubricating oils for spark-ignited and compression-ignited internal combustion engines, including automobile and truck engines, two-cycle engines, aviation piston engines, marine and railroad diesel engines, and the like. Also contemplated are lubricants for gas engines, stationary power engines and turbines and the like. Transaxle lubricants, gear lubricants, metal-working lubricants and other lubricating oil and grease compositions, as well as functional fluids such as hydraulic fluids and automatic transmission fluids, benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale oil can also be included as the base oil. Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di(2-ethylhexyl)benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic oils. These are exemplified by the oils prepared through polymerization of ethylene oxide or propylene oxide, the alkyl and aryl ethers of these polyoxyalkylene polymers (e.g. methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another class of synthetic oils (e.g., tetraethyl silicate, tetraisopropyl silicate, tetra-(2-ethylhexyl)silicate, tetra-(4-methyl-2-ethylhexyl)silicate, tetra-(p-tert-butylphenyl)silicate, hexa-(4-methyl-2-pentoxy)-disiloxane, poly(methyl)siloxanes, poly(methylphenyl)-siloxanes, etc.). Other synthetic oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricants and functional fluids of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants and functional fluids of the present invention contain an amount of the composition of this invention sufficient to provide it with antioxidant and improved extreme pressure properties. Normally this amount will be about 0.25% to about 10%, preferably about 0.4% to about 7.5%, of the total weight of the fluid.

The invention also contemplates the use of other additives in combination with the compositions of this invention. Such additives include, for example, detergents and dispersants of the ash-producing or ashless type, corrosion- and auxiliary oxidation-inhibiting agents, pour point depressing agents, auxiliary extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-beta-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Pat. No. 1,306,529 and in many U.S. Pat. Nos. including the following:

| | | |
|---|---|---|
| 3,163,603 | 3,351,552 | 3,541,012 |

| -continued | | |
|---|---|---|
| 3,184,474 | 3,381,022 | 3,542,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | Re 26,433 |
| 3,346,493 | 3,522,179 | |

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants." The materials described in the following U.S. Pat. Nos. are illustrative:

| | |
|---|---|
| 3,413,347 | 3,725,480 |
| 3,697,574 | 3,726,882 |
| 3,725,277 | |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Auxiliary extreme pressure agents and corrosion- and auxiliary oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, poly-propylene (molecular weight 500)-substituted phenyl phosphite, diisobutyl-substituted phenyl phosphite; and metal thiocarbamates, such as zinc dioctyldithiocarbamate and barium heptylphenyl dithiocarbamate.

The compositions of this invention can be added directly to the lubricant. Often, however, they are preferably diluted with a substantially inert, normally liquid organic diluent such as mineral oil, naphtha, benzene, toluene or xylene, to form an additive concentrate. These concentrates usually contain from about 20% to about 90% by weight of the composition of this invention and may contain, in addition, one or more other additives known in the art or described hereinabove.

The following is an exemplary hydraulic fluid in accordance with this invention.

| Ingredient | Parts by Weight |
|---|---|
| Mineral oil | 94.25 |
| Product of Example 1 | 1.50 |
| Pentaerythritol ester of polybutenyl (mol. wt. about 1000) succinic acid, reacted with alkylene polyamine | 1.43 |
| Reaction product of alkylene polyamine with polybutenyl (mol. wt. about 1700) succinic anhydride containing more than one succinic group per polybutenyl group | 1.25 |
| Basic magnesium petroleum sulfonate | 0.39 |
| Basic sulfurized calcium tetrapropenyl phenate | 1.18 |
| Silicone anti-foam agent | 0.01 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A composition comprising (A) a mixed metal salt of (A)(I) at least one acid of formula I

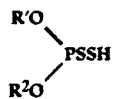

wherein $R'$ and $R^2$ are the same or different and each of $R'$ and $R^2$ is a hydrocarbon-based radical, and (A)(II) at least one aliphatic or alicyclic carboxylic acid containing from about 2 to about 40 carbon atoms; the ratio of equivalents of (A)(I) to (A)(II) being in the range of about 0.5:1 and about 400:1, and (B) at least one sulfurized Group II metal phenate; the weight ratio of (A) to (B) being in the range of about 40:1 to about 1:2.

2. The composition of claim 1 wherein the metal for component (A) is at least one of Group I metals, Group II metals, aluminum, tin, cobalt, lead, molybdenum, manganese and nickel.

3. The composition of claim 1 wherein each of $R'$ and $R^2$ is an alkyl radical containing from about 3 to about 50 carbon atoms.

4. The composition of claim 1 wherein each of $R'$ and $R^2$ is a branched alkyl radical.

5. The composition of claim 1 wherein the metal for component (A) is zinc.

6. The composition of claim 1 wherein component (A)(II) has the formula $R^3COOH$, wherein $R^3$ is an aliphatic or alicyclic hydrocarbon-based radical.

7. The composition of claim 1 wherein component (A)(II) contains from about 2 to about 40 carbon atoms.

8. The composition of claim 6 wherein $R^3$ is a saturated aliphatic radical.

9. The composition of claim 6 wherein $R^3$ is a branched alkyl radical.

10. The composition of claim 6 wherein each of $R'$ and $R^2$ is 2-ethylhexyl and $R^3$ is 3-heptyl.

11. The composition of claim 1 wherein the ratio of equivalents of (A)(I) to (A)(II) is between about 0.5:1 and 200:1.

12. The composition of claim 1 wherein the ratio of equivalents of (A)(I) to (A)(II) is between about 0.5:1 and about 100:1.

13. The composition of claim 1 wherein the ratio of equivalents of (A)(I) to (A)(II) is between about 0.5:1 and about 50:1.

14. The composition of claim 1 wherein the ratio of equivalents of (A)(I) to (A)(II) is between about 0.5:1 and about 20:1.

15. The composition of claim 1 wherein the ratio of equivalents of (A)(I) to (A)(II) is between about 0.5:1 and about 4.5:1.

16. The composition of claim 1 wherein the ratio of equivalents of (A)(I) to (A)(II) is between about 2.5:1 and about 4.25:1.

17. The composition of claim 1 wherein component (B) includes at least one hydrocarbon-based radical attached to an aromatic moiety, said hydrocarbon-based radical having from about 6 to about 80 carbon atoms.

18. The composition of claim 17 wherein said hydrocarbon-based radical of component (B) has from about 6 to about 30 carbon atoms.

19. The composition of claim 17 wherein said hydrocarbon-based radical of component (B) has from about 8 to about 25 carbon atoms.

20. The composition of claim 17 wherein said hydrocarbon-based radical of component (B) has from about 8 to about 15 carbon atoms.

21. The composition of any of claims 17–20 wherein said aromatic moiety is a benzene nucleus.

22. The composition of claim 1 wherein component (B) contains up to about 1000% of the metal present in the corresponding sulfurized normal Group II metal phenate.

23. The composition of claim 1 wherein component (B) contains up to about 500% of the metal present in the corresponding sulfurized normal Group II metal phenate.

24. The composition of claim 1 wherein component (B) contains from about 250% to about 450% of the metal present in the corresponding sulfurized normal Group II metal phenate.

25. The composition of claim 1 wherein component (B) has a phenol group to sulfur mole ratio in the range of about 2:1 to about 1:2.

26. The composition of claim 1 wherein component (B) has a phenol group to sulfur mole ratio in the range of about 2:1 to about 1:1.

27. The composition of claim 1 wherein component (B) has a phenol group to sulfur mole ratio of about 4:3.

28. The composition of claim 1 wherein the ratio (A) to (B) is in the range of about 20:1 to about 1:1.

29. The composition of claim 1 wherein the ratio of (A) to (B) is from about 15:1 to about 5:1.

30. The composition of claim 1 wherein component (B) is basic sulfurized calcium propylene tetramer phenate.

31. The composition of claim 1 wherein the Group II metal in component (B) is calcium.

32. An additive concentrate comprising a substantially inert, normally liquid organic diluent and the composition of any of claims 1-20 or 22-31.

33. An additive concentrate comprising a substantially inert, normally liquid organic diluent and the composition of claim 21.

34. A lubricant or functional fluid comprising a major amount of a lubricating oil and a minor amount of the composition of any of claims 1-20 or 22-31.

35. A lubricant or functional fluid comprising a major amount of a lubricating oil and a minor amount of the composition of claim 21.

* * * * *